United States Patent [19]
Vos

[11] Patent Number: 5,275,942
[45] Date of Patent: Jan. 4, 1994

[54] MAMMALIAN CELL-BASED DNA LIBRARIES

[75] Inventor: Jean-Michel H. Vos, Chapel Hill, N.C.

[73] Assignee: The University of North Carolina at Chapel Hill, Chapel Hill, N.C.

[21] Appl. No.: 808,511

[22] Filed: Dec. 16, 1991

[51] Int. Cl.⁵ .............................. C12N 15/09
[52] U.S. Cl. .................. 435/172.3; 435/252.3; 435/320.1; 536/23.5
[58] Field of Search ............... 435/252.3, 320.1, 172.3

[56] References Cited

U.S. PATENT DOCUMENTS 4,686,186  8/1987  Sugden .............................. 435/243

OTHER PUBLICATIONS

W. Hammerschmidt and B. Sugden, *Cell* 55, 427–433 (1988).
W. Hammerschmidt and B. Sugden, *Nature* 340, 393–397 (1989).
J.-M. Vos et al., *Molecular Carcinogenesis* 2, 237–244 (1989).
J-M. Vos and P. Hanawalt, *Mutation Research* 220, 205–220 (1989).

*Primary Examiner*—Robert J. Hill, Jr.
*Assistant Examiner*—John D. Ulm
*Attorney, Agent, or Firm*—Bell, Seltzer, Park & Gibson

[57] ABSTRACT

A recombinant plasmid useful for the production of large-insert, stably maintained, episomes in mammalian cells is disclosed, along with cells, DNA libraries, and methods of using the same. The plasmid comprises a lymphotrophic herpes virus segment (e.g., an Epstein-Barr virus segment) containing an origin of plasmid replication (oriP) and a heterologous insert segment linked to the lymphotrophic herpes virus segment. The heterologous insert segment has a length of at least 100 kilobases. In a preferred embodiment, the lymphotrophic herpes virus segment is capable of producing infectious virions in a suitable host cell, and the lymphotrophic herpes virus segment has regions deleted so that the recombinant plasmid retains the capability of producing infectious virions in the host.

48 Claims, 7 Drawing Sheets

MAMMALIAN CELL-BASED DNA LIBRARIES

FIELD OF THE INVENTION

The present invention relates to libraries of large DNA inserts carried in mammalian cells, infectious virions for producing such libraries, recombinant plasmids for producing such virions, and assays for determining the infectivity of such virions.

BACKGROUND OF THE INVENTION

The characterization of the structure of human chromosomes and elucidation of their various encoded activities are major interests of modern biology and medicine. The past decade and a half in molecular biology has been a time of "hit-and-run" approach for cloning, sequencing, and analyzing individual genes of specific interest. However, there is a need for an overall and comprehensive approach to the study of human chromosomes. For example, of the estimated 100,000 human genes, only some 3,000 are represented as sequenced genes, mapped markers, cloned fragile sites, and neoplastic breakpoints. V. McKusick, *N. Eng. J. Med.* 320: 910–915 (1989). Much less is known about chromosomal regions with other basic functions such as DNA replication, chromatin packaging, and chromosomal segregation. Thus, for progress in human physiology and pathology, it would be extremely valuable to have a complete physical map and nucleotide sequence of the human genome.

The recent construction of a detailed linkage map of the human genome in size of 1–10 megabases is an important first step for the localization of genes and other functional chromosomal regions. H. Donis-Keller et al., *Cell* 51: 319–317 (1987). To increase the resolution of such a map in a range suitable for rapid cloning and sequencing, an average spacing of 100 Kb has been estimated, which required the mapping of 30,000 linearly ordered human DNA clones. M. Olson et al., *Science* 245: 1434–1435 (1989). To construct such a physical map with 100 Kb resolution, new mapping approaches such as the Sequence-Tagged-Sites (STS) and Repetitive-Sequence-Fingerprinting based mapping methodologies (RSF) are being developed to allow computer-mediated storage and retrieval of specific and unique human sequences. See M. Olsen et al., supra; R. Stallings et al., *Proc. Natl. Acad. Sci. USA* 87: 6218–6222 (1990). However, with respect to the 100 Kb resolution that will be required for such a map with good practical coverage, a key problem is finding a vector with suitable capacity.

Common cloning systems allow human DNA inserts to be propagated in bacteria or yeast. A problem with the bacterial cosmid system, however, is that it only has limited cloning capacity (about 40 Kb). Two newly developed prokaryotic vectors, the P1 cloning system and the mini-F based plasmid vector, provide the opportunity to propagate larger DNA fragments in bacteria. See N. Sternberg et al., *Proc. Natl. Acad. Sci. USA* 87: 103–107 (1990); M. O'Connor et al., *Science* 244: 1307–1313 (1989). The P1 cloning system can clone up to 100 Kb DNA and the mini-F based plasmid vector has the potential for cloning 136 Kb DNA. Yeast artificial chromosome (YAC) has capacity for carrying exogenous DNA fragments in the megabase range. D. Burke et al., *Science* 236: 806–812 (1987). A problem with these systems is that human genomic DNA propagated in heterologous organisms such as bacteria or yeast can be subjected to sequence reorganization, particularly if carrying highly repetitive sequences such as SINEs, LINEs or VNTRs. Furthermore, human genetic imprinting such as 5-methylcytosine will not be maintained faithfully in these single cell organisms.

Accordingly, there is a need for a cloning system which accomodates large size inserts, and which can be used in mammalian, particularly human, cells. The present invention is based on continuing research into solutions to this problem.

SUMMARY OF THE INVENTION

A first aspect of the present invention is a recombinant plasmid useful for the production of large-insert, stably maintained, episomes in mammalian cells. The plasmid comprises a lymphotrophic herpes virus segment (e.g., an Epstein Barr virus segment) containing an origin of plasmid replication (oriP) and a heterologous insert segment linked to the lymphotrophic herpes virus segment. The heterologous insert segment has a length of at least 100 kilobases. In a preferred embodiment, the lymphotrophic herpes virus segment is capable of producing infectious virions in a suitable host cell, and the lymphotrophic herpes virus segment has regions deleted so that the recombinant plasmid retains the capability of producing infectious virions in the host.

A second aspect of the present invention is a method for transforming mammalian cells. The method comprises transfecting a mammalian cell with a recombinant plasmid as given above. In a preferred embodiment, the transfecting step is carried out by lipofection.

A third aspect of the present invention is a transformed mammalian cell containing a recombinant plasmid as given above as a large-insert, stably maintained episome.

A fourth aspect of the present invention is a large-insert DNA library comprising a plurality of transformed mammalian cells. Each of the transformed mammalian cells contains a recombinant plasmid as given above. The heterologous insert segment linked to the lymphotrophic herpes virus segment has a length of at least 100 kilobases and comprising a member of the DNA library.

A fifth aspect of the present invention is a large-insert DNA library comprising a plurality of infectious lymphotrophic herpes virus virions. Each of the virions contains a recombinant DNA sequence, the recombinant DNA sequence comprising a lymphotrophic herpes virus segment capable of infecting mammalian cells and producing infectious virions in a suitable host, and a heterologous insert segment linked to the lymphotrophic herpes virus segment. The heterologous insert segment has a length of at least 100 kilobases and comprises a member of the DNA library; the lymphotrophic herpes virus segment has regions deleted so that the recombinant DNA sequence retains the capability of producing infectious virions in a suitable host.

The foregoing and other objects and aspects of the present invention are discussed in detail in the drawings herein and the specification below.

DETAILED DESCRIPTION OF THE INVENTION

Figure 1:
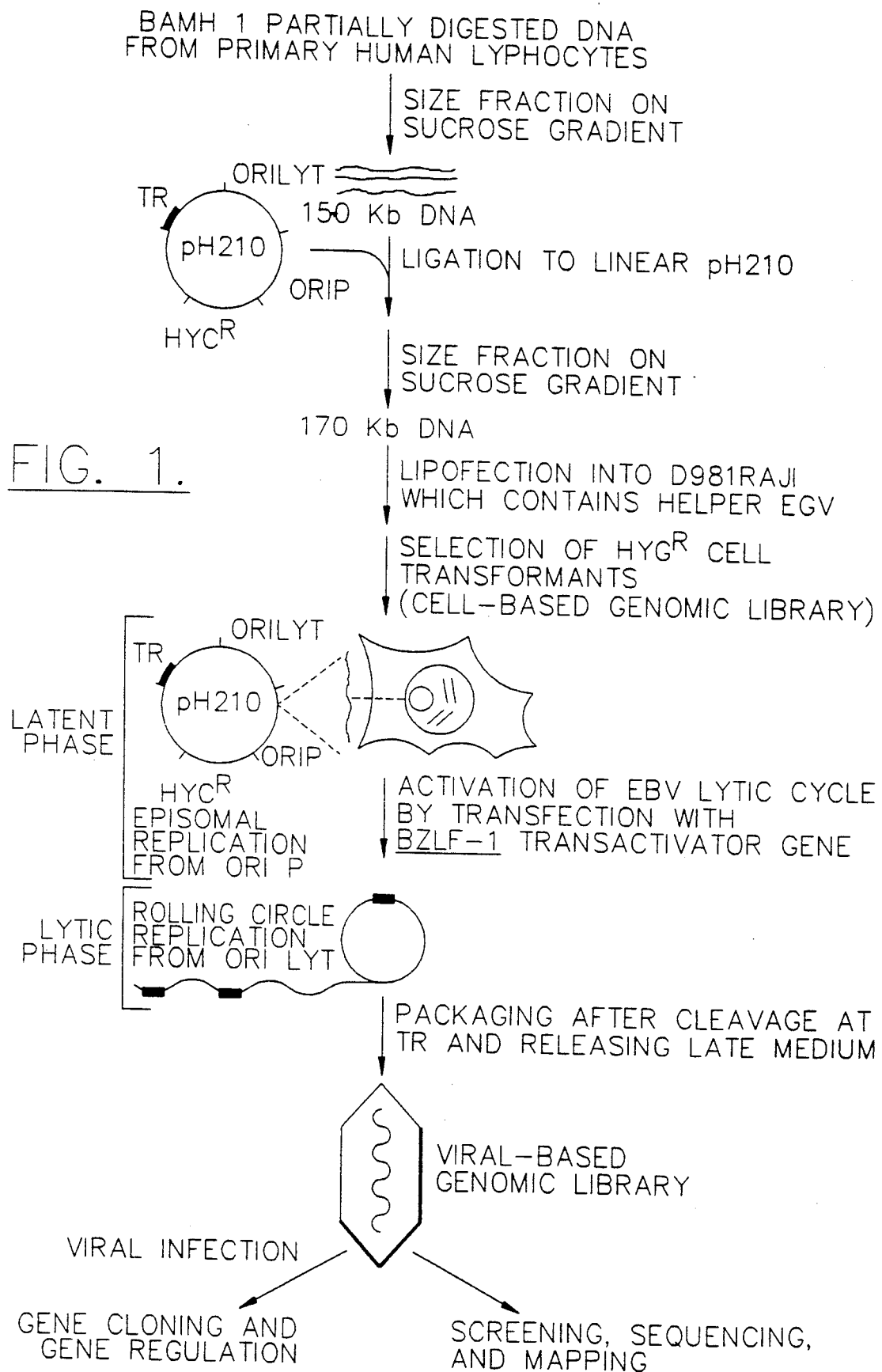
FIG. 1 schematically illustrates the construction of an EBV-based human large size insert genomic library.

As noted above, the present invention provides recombinant plasmids useful for the production of large-insert stably maintained episomes in mammalian cells, and for the production of large-insert genomic DNA libraries. The plasmids comprise a lymphotrophic herpes virus segment containing an origin of plasmid replication (oriP), and a heterologous insert segment linked to the lymphotrophic herpes virus segment.

The heterologous insert segment has a length of at least 100 kilobases, and may have a length of at least 120 or even 150 kilobases. The upper limit on the length of the heterologous DNA insert depends on whether or not it is desired to produce infectious virions containing the insert. If infectious virions are to be produced the heterologous DNA will be limited to a length which can be encapsidated in the virion: this will depend on the size of the lymphotrophic herpes virus segment, as discussed in greater detail below, but will typically be up to about 160, 180, or 200 kilobases.

When the recombinant plasmid is to be used for the production of infectious virions, the lymphotrophic herpes virus segment is constructed so as to be capable of producing infectious virions in a suitable host cell, and should have regions deleted so that the recombinant plasmid retains the capability of producing infectious virions in the host. Typically, the lymphotrophic herpes virus segment has regions deleted which render the recombinant plasmid capable of producing infectious virions only in a host cell containing helper sequences (or "helper cells"). Suitable helper cells are known, as discussed in greater detail below.

The lymphotrophic herpes virus segment employed in carrying out the present invention preferably comprises an Epstein-Barr virus segment. Epstein-Barr virus (EBV), a human herpesvirus, is one of the largest human viruses with a genome of 172 Kb. EBV DNA can be stably maintained in cells as episomes during its latent phase and amplified and packaged as infectious virions during the lytic phase. E. Kieff and D. Liebowitz, in B. Fields (ed), *Virology*. Raven Press, Ltd., New York, pp. 1889-1920 (1990). If they are to be used for producing infectious virions, EBV plasmid vectors require the EBV origin of plasmid replication (or "oriP"), the EBV lytic origin of replication ( or "oriLyt") for induction of the lytic phase and mediation of viral reproduction, and the fused long terminal repeat region (or "TR"), for the DNA cleavage and packaging functions. These regions are known. EBV Plasmids containing oriP are disclosed in U.S. Pat. No. 4,686,186 to W. Sugden (the disclosure of this and all other patent references cited herein are incorporated herein by reference). The EBV oriLyt region is disclosed in W. Hammerschmidt and B. Sugden, *Cell* 55: 427-33 (1988). The EBV "TR" region is disclosed in W. Hammerschmidt and B. Sugden, *Nature* 340: 393-397 (1989). It will be appreciated by those skilled in the art that other lymphotrophic herpes viruses may also be used in practicing the invention described herein in like manner as EBV.

In one embodiment of the invention the heterologous insert segment includes a centromere operable in the host cell. This provides for stable maintenance of the plasmid in the transformed host cell and the progeny thereof. Additional coding sequences may also included in the heterologous segment, such as a promoter operable in the host cell and a sequence encoding a protein or peptide operably associated with the promoter. The centromere may be of any suitable species, but is typically mammalian (e.g., human), in origin. Transformed host cells containing a centromere can be conveniently identified by growing the cells in culture without a selectable marker such as hygromycin: transformed cells will be rendered stable over time by the provision of the operable centromere in the recombinant plasmid.

Methods for transforming mammalian cells provided herein involve transfecting a mammalian cell, preferably a human cell, with a recombinant plasmid as given above. Preferably the mammalian cells to be transformed are grown as a monolayer in in vitro cell culture, and the transfecting step is carried out by lipofection in accordance with known techniques. Suitable mammalian cells include B-lymphoblastoid cells such as the RAJI cell line (a known helper cell line), epithelial cells such as the D98 cell line, and fusions of a mammalian epithelial cell and a mammalian B-lymphoblastoid cell such as D98/RAJI cells. Fusions of suitable cell lines can be carried out in accordance with known techniques. The cells may optionally be immortal, as is the case with the D98 cell line and D98/RAJI cells. If infectious virions are to be produced from the transformed cells then the mammalian cells should be a suitable host for producing infectious virions (i.e., a helper cell); otherwise, they need not.

As noted above, the present invention provides for genomic DNA libraries, particularly a human genomic DNA library, including both partial and complete genomic DNA libraries. Given a library with average insert size of 160 Kb, approximately 90,000 clones are required to provide a five-hit coverage of the entire human genome with a >99% probability of containing any single copy sequence. D. Burke, *Gen. Anal. Tech. Appl.* 75: 94-99 (1990). Single chromosome libraries or subclones of YAC-based libraries with large genomic inserts may also be established using this EBV-based cloning system. Since the cloning system of the present invention allows one to propagate DNA inserts in mammalian cells, and particularly human cells, human genetic imprinting such as DNA methylation patterns should be preserved faithfully in the genomic DNA inserts; functional assays may be conducted to study gene expression or to identify defective genes from human syndromes with a library of the present invention.

The steps involved in constructing one illustrative EBV-based library of large-sized fragments of human genomic DNA is schematically illustrated in FIG. 1. These steps are as follows:

Isolation of High Molecular Weight Human Genomic DNA

High molecular weight (HMW) human genomic DNA of 150-200 kb is isolated from primary human lymphocytes following the standard sucrose step-gradient procedure developed for construction of YAC libraries. Briefly, cells from 40 ml of blood samples are gently lysed with 3% SDS and HMW DNA is purified from other cell components by centrifugation through a step-wise 15%-20%-50% sucrose gradient. The size distribution of the DNA is checked by Pulse Field Gel Electrophoresis (PFGE) using the CHEF system in accordance with known techniques. At all stages, care is taken in manipulating the large size DNA (cut tips, etc.).

Partial Digestion of HMW DNA

Partial BamHI digestion of the HMW DNA is performed by serial dilution of the restriction enzyme. For example, 50-100 μg genomic DNA is prepared per reaction. Partially restricted DNA of 150-200 kb average size is size-selected by isokinetic sucrose gradient centrifugation as described above. This latter size fractionation step is particularly important in the construction of large size genomic libraries. The DNA size distribution before and after the sucrose gradient is assayed by PFGE as above.

Ligation to the mini EBV Vector 50-100 μg of BamHI-linearized and AP-dephosphorylated pH210 plasmid DNA is ligated to an equal weight of partially restricted human genomic DNA by 16 hours incubation with T4 ligase. The ligation products of 150-200 kb average size are then size-selected by isokinetic sucrose gradient centrifugation as above. The DNA size distribution before and after the sucrose gradient is also verified by PFGE.

Cell Transformation

The ligated 150–200 kb genomic DNA is transfected into the human lymphoblastoid helper cell line D98/RAJI by lipofection in accordance with known techniques. Stable cell transformants are selected by growing the transfected cells in the presence of 400 µg/ml hygromycin for 2–3 weeks (see J.-M. Vos et al., *Mol. Carc.* 2, 237–244 (1989)). At that point, stocks of $10^7$ cells are frozen and kept in liquid nitrogen for future usage.

Episomal Human Genomic Library

Episomal DNA is extracted by the Hirt procedure in accordance with known techniques (See J.-M. Vos and J. Rommelaere, *Mol. Cell. Biol.* 9, 2897–2905 (1987)). The average size of episomal clones is analyzed by PFGE using circular EBV genome as marker. In the alternative, the DNA is linearized by random breakdown with ionizing radiation or by restriction with an infrequent cutter which linearizes plasmid pH210, i.e., NotI or SfiI, and the linearization products analyzed by PFGE. If necessary, the miniEBV-based episomes are distinguished from the endogenous EBV helper DNA by Southern hybridization with miniEBV-specific probes, i.e., Hygromycin.

Production of Viral Libraries

To produce EBV virus carrying human genomic DNA of 150–200 kb average size, the cell-based episomal libraries established with the miniEBV vector pH210 in the D98/RAJI lymphoblastoid cells is used. The lytic cycle of the resident EBV helper virus is induced by a variety of means, such as transfection of the cell-based libraries with the BZLF-1 transactivator gene, see J. Countryman and G. Miller, *Proc. Natl. Acad. Sci. USA* 82: 4085–4089 (1985), or treatment of the cell-based libraries with 20 ng/ml of 12-O-tetradecanoyl-13-acetate (TPA) for four days at a concentration of $10^6$ cells/ml.

Recovery of EBV Libraries

The virus released in the medium is purified from cell debris by filtration through 0.2 µm membrane and concentrated by pelleting at 47 krpm. To eliminate non-encapsidated DNA, the viral stock is further treated with DNAse I at 10 µg/ml for ½ hour RT, followed by pelleting through a 25% sucrose cushion at 24 krpm for one hour. Viral stocks are stored in RPMI medium with 10% serum at −70° C.

Infectivity of Viral Stocks

Concentration of the viral stock is measured by a rapid blot hybridization method using alkalilyzed virions and a plasmid-specific probe in accordance with known techniques. See J.-M. Vos and J. Rommelaere, supra. Infectivity of the viral library stocks is measured as follows: to pellets of lymphoblastoid D98/RAJI cells ($5 \times 10^4$ cells) 500 µl of serial dilution of the viral library is added and incubated for two hours at 37° C. with gentle shaking. Cells are then transferred into 24-well dishes (6 wells per dilution) and selected with 300 µg/ml of hygromycin B. The concentration of the viral library is then determined by the fraction of wells with hygromycin resistant cells as a function of viral library dilutions. See, e.g., B. Sugden et al., *Mol. Cel. Biol.* 5, 410–413 (1985).

Viral-based Genomic Library

Encapsidated DNA is purified by lysis on 0.5% SDS and gentle extraction with phenol/chloroform, followed by dialysis against TE pH8 and vacuum concentration. Since the encapsidated DNA is linear, the average size of the inserts is measured by PFGE using a ladder of ligated bacteriophage lambda DNA as MW standard. To distinguish the helper EBV, Southern hybridization may be performed with a pH210-specific probe.

The present invention is explained in greater detail in the following non-limiting Examples. As used herein, "cm" means centimeters, "mm" means millimeters, "kb" means kilobases, "µg" means micrograms, "ng" means nanograms, "mmol" means millimoles, "U" means units, "rpm" means revolutions per minute, "krpm" means thousand revolutions per minute, "RPMI" means Roswell Park Memorial Institute, "V" means volts, "µF" means microFarads, "Ci" means Curies, "RT" means room.temperature, and temperatures are given in degrees Centigrade unless otherwise indicated.

EXAMPLE 1

Plasmid Preparation

Figure 2:
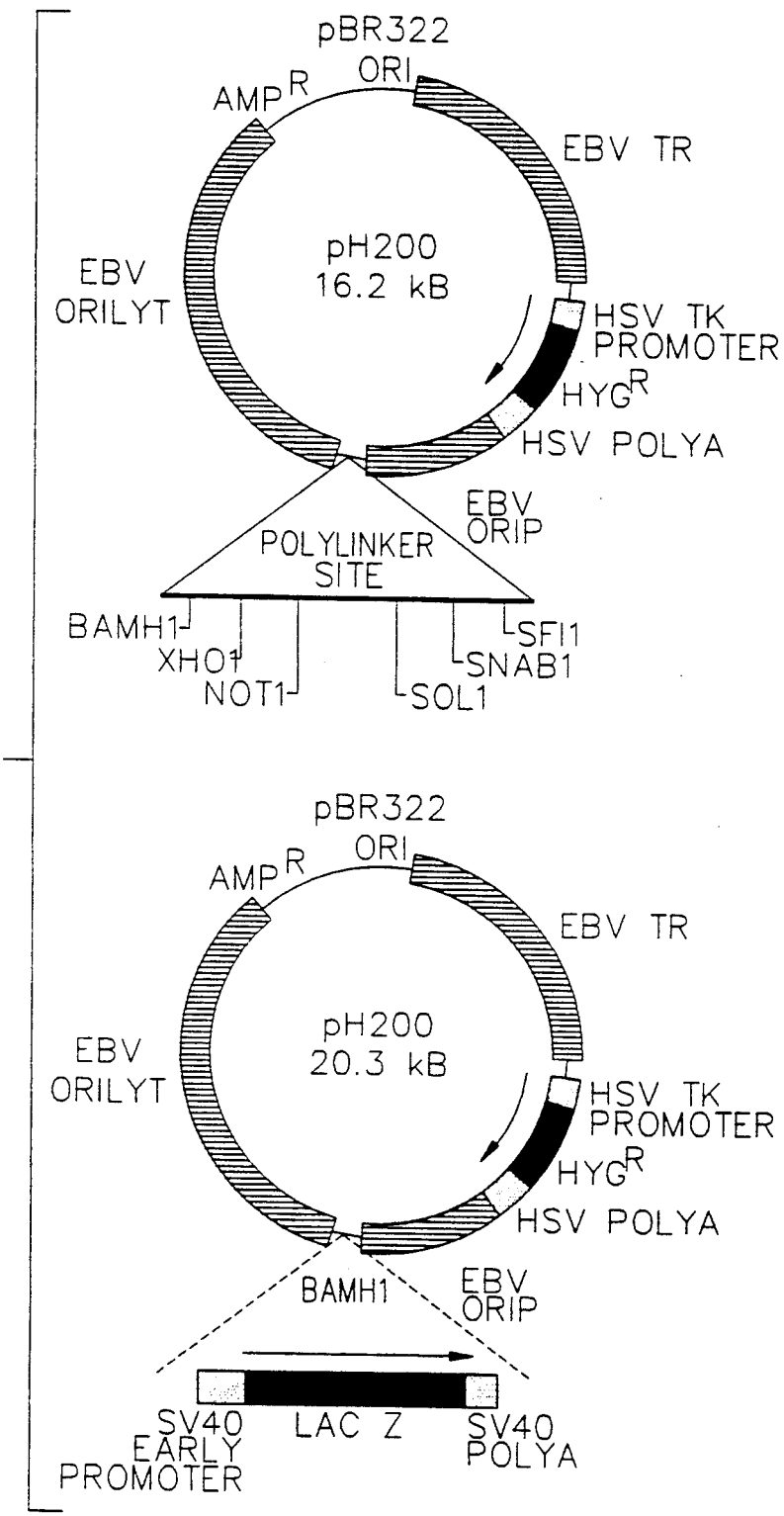
FIG. 2 shows the structures of the episomal forms of plasmids pH200 (16.2 kb) and pH210 (20.4 kb). The EBV-derived latent and lytic origins of replication and terminal repeats are shown, as well as the pBR322 section and the selectable hygromycin gene and screenable lacZ gene.

The EBV plasmid p588 was provided by William M. Sugden (McArdle Cancer Center, University of Wisconsin). p588 contains oriP, oriLyt, and the TR region of EBV on a pBR322 backbone. Mini EBV plasmid pH200 was produced from p588 by inserting a polylinker site therein; Mini EBV plasmid pH210 was produced from p588 by adding the lacZ (bacterial β-galactosidase) gene thereto. Plasmids pH200 and pH210 are shown in FIG. 2. Plasmids were purified by two rounds of CsCl-ethidium bromide gradient centrifugation in accordance with known techniques. See D. Moore, in F. Ausubel et al., (eds), *Current protocols in molecular bioloy.* John Wiley & Sons, Inc., New York, pp. 1.7.1–1.7.7 (1989). The plasmid pH210 has been deposited with the American Type Culture Collection, 12301 Parklawn Drive, Rockville, Md. 20852 USA, in accordance with the provisions of the Budapest Treaty, on Dec. 5, 1991, and has been assigned ATCC Accession Number 75171.

EXAMPLE 2

Establishment of Stably Expressed Mini-EBV DNA in Helper Cells

The mini-EBV plasmid pH200 and the modified mini-EBV plasmid pH210 described in Example 1 above were introduced into EBV-transformed B-lymphoblastoid HH514 cells by electroporation. Three days after electroporation hygromycin was added, and three weeks after electroporation hygromycin-resistant cell transformants were selected for stable maintenance of the mini-EBV.

HH514 is an EBV-transformed B-lymphoblastoid cell line. M. Rabson et al., *Proc. Natl. Acad. Sci. USA* 80: 2762–2766 (1983). HH514 cells were grown in RPMI-1640 medium with 10% fetal bovine serum (FBS). Electroporation was carried out with a BioRad Gene Pulser with voltage and capacitor set at 200 V and 960 µF. $5 \times 10^6$ exponentially grown HH514 cells and 20 µg of plasmid DNA were mixed in 0.3 ml of complete growth medium in a 0.4 cm electroporation cuvette (BioRad) and incubated on ice for 10 minutes. After electroporation, cells were incubated on ice for another 10 minutes, then seeded into 10 ml of complete growth medium, and incubated at 37° C. Three days after electroporation, hygromycin was added to a final concentration of 200-400 μg/ml to select for stable cell transformants as described above.

EXAMPLE 3

FACS Analysis of LacZ+ Cell Transformants

Figure 3:
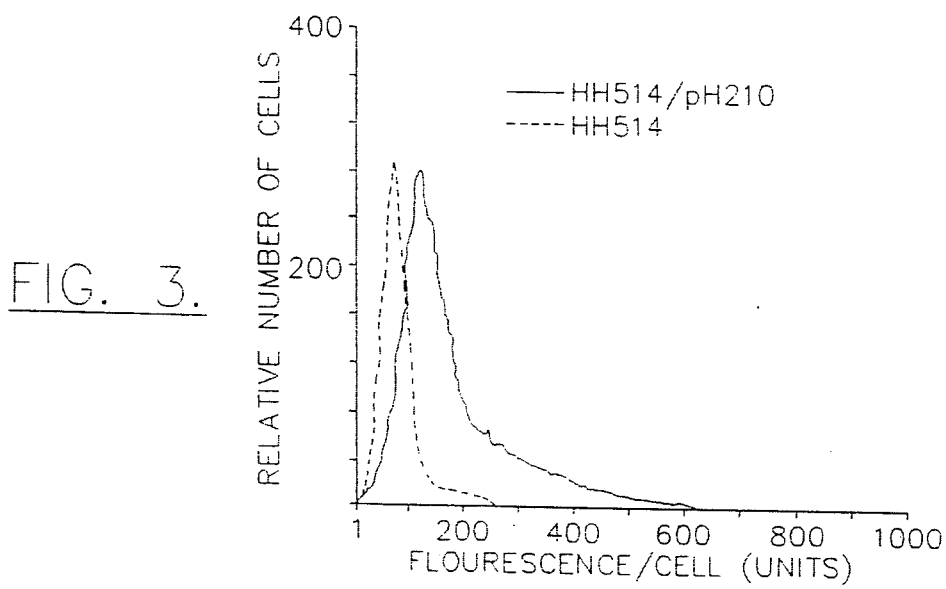
FIG. 3 shows a FACS analysis of the mini EBV/lacZ (plasmid pH210) transformed lymphoblastoid helper cells (HH514). HH514 were transformed with mini EBV/lacZ DNA by electroporation and cell transformants were selected as hygromycin-resistant cells. Cells were loaded with FDG at 37° C. and allowed to generate fluorescein at 4° C. HH514 cells were used as negative control.

The expression of the lacZ gene carried on the mini-EBV pH210 in hygromycin-resistant HH514 cells produced as described in Example 2 above was verified by staining cells with the β-galactosidase substrate fluorescein di-β-D-galactopyranoside (FDG; Molecular Probes, Inc.) and sorting lacZ positive cells by FACS. Cells were loaded with FDG at 37° C., allowed to generate fluorescein at 4° C., and analyzed with FACS in accordance with known techniques. See, e.g., G. Nolan et al., *Proc. Natl. Acad. Sci. USA* 85: 2603-2607 (1988). HH514 cell were used as a negative control. As shown in FIG. 3, pH210-transformed HH514 lacZ positive cells developed strong fluorescence as indicated by a shifted peak to a higher fluorescence level, whereas HH514 lacZ negative cells did not develop appreciable fluorescence. This analysis indicated that 75% of hygromycin-resistant cells and only 2% of HH514 control cells were sorted as lacZ+. Thus, most hygromycin-resistant cells stably express mini-EBV pH210.

EXAMPLE 4

Preparation of EBV Virions pH200 transformed HH514 cells were selected as 200 μg/ml and 400 μg/ml hygromycin resistant cells (HYG$^R$ 200 μg/ml and HYG$^R$ 400 μg/ml). To demonstrate packaging of mini-EBV DNA, we analyzed the DNA in EBV virions produced from plasmid-transformed cells after induction of the EBV lytic phase.

The lytic phase of EBV in mini EBV-transformed HH514 cells was induced by either transfection with the viral transactivator gene BZLF-1 (J. Countryman and G. Miller, *Proc. Natl. Acad. Sci. USA* 82: 4085-4089 (1985)) expressed from a CMV promoter (S. Kenney et al., *J. Virol.* 63: 1729-1736 (1989)), or by incubation with 20 ng/ml of 12-O-tetradecanoylphorbol-13-acetate (TPA; Sigma)(H. Zur. Hausen et al., *Nature* 272: 373-375 (1978)), or by 20 ng/ml TPA and 1 mM sodium butyrate (Sigma)(A. Saemundsen et al., *Virology* 107: 557-561 (1980)). Transfection with the viral transactivator gene BZLF-1 was preferred. Five days after induction, supernatants were collected, treated with 20 U/ml DNaseI (Sigma) to destroy non-packaged DNA, and centrifuged at 11,000 rpm for 2 hours in a SS34 rotor (Sorval, Inc.) to pellet virions. The packaged linear DNA was isolated from virions by proteinase K digestion and purified by phenol extraction, digested with BamHI, which cleaves pH200 at one site, and subjected to Southern blot analysis with a plasmid-specific probe.

Figure 4:
FIG. 4 shows the production of EBV virions carrying plasmid-derived DNA. The lytic phase of EBV in pooled cell transformants was induced under the conditions indicated on the top of the figure. Five days later, the virions released into medium were purified. DNA extracted from purified virions was subjected to Southern blot analysis with a plasmid-specific probe (HYG$^R$ resistant gene). The position of unrestricted packaged DNA and linear monomeric plasmid pH200 are indicated as pH200 (V) and pH200 (M), respectively. 10, 100 pg of BamH1 digested pH200 plasmid DNA was used as monomer standard. DNA in lane 12 was partially digested, giving a faint ladder between pH200 (V) and pH200 (M).

As shown in FIG. 4, plasmid-derived DNA, which migrated at the position of the linear monomeric plasmid after BamHI digestion, was indeed packaged into virions. In addition, the unrestricted plasmid-derived DNA migrated much slower than the linear monomeric plasmid, indicating that the packaged DNA was much larger than the original 16 Kb plasmid. The EBV virions produced after the combination of TPA and butyrate treatments carried the highest amount of plasmid-derived DNA.

EXAMPLE 5

Analysis of Packaged Plasmid DNA by Pulse Field Gel Electrophoresis

The sizes of packaged plamid-derived DNA were determined directly by pulse field gel electrophoresis (PFGE), which can resolve large DNA fragments. See generally D. Schwartz and C. Cantor, *Cell* 37: 67-75 (1984). PFGE was carried out on a CHEF apparatus (G. Chu et al., *Science* 234: 1582-1585 (1986)) in 1% agarose and 0.5×TBE at 200 V for 20 hours at a switching time of 15 seconds. After electrophoresis, DNA was transferred from agarose gels to nitrocellulose membrane in accordance with known techniques. See E. Southern, *J. Mol. Biol.* 98: 503-517 (1975). DNA probes were labeled with [α-P$^{32}$]dCTP (NEN, 3000 Ci/mmol) using a nick translation kit (Promega). The plasmid pBR322 was used to detect vector-specific sequence, whereas EBV EBNA-1 sequence was used to detect helper EBV DNA. After hybridization, radioactive DNA signals were detected by autoradiography.

Figure 5:
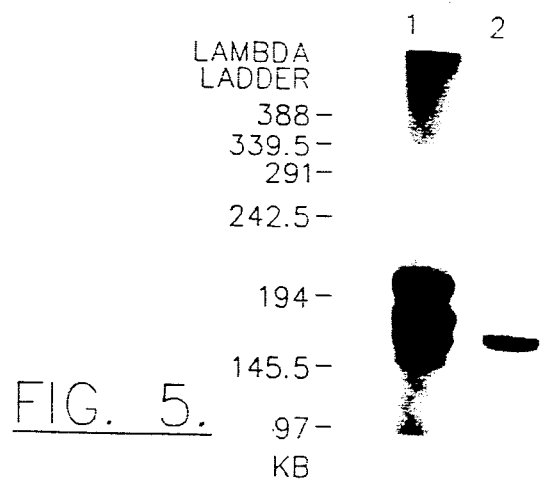
FIG. 5 shows the determination of the sizes of packaged plasmid DNA by Pulse-Field Gel Electrophoresis (PFGE). The EBV virions were prepared from pH200-transformed HH514 cells. DNA extracted from purified virions was subjected to PFGE. Plasmid pH200- and EBV-DNA were separately detected by Southern Blot analysis with pBR322 (lane 1) and EBNA-1 (lane 2) as probes, respectively. The molecular weight marker was ligated lambda DNA concatemers.

As shown in FIG. 5, the packaged plasmid-derived DNAs (lane 1) migrated as a ladder of bands ranging in sizes from 150 to 200 Kb. Since the packaged plasmid DNA had a size of 150-200 Kb, there should be 9- to 12-mer of 16 Kb plasmid DNA packaged into virions. That is in the size range of the 160 Kb helper EBV genome. See K. Jeang and S. Hayward, *J. Virol.* 48: 135-148 (1983).

EXAMPLE 6

Packaging of Unrearranged Mini-EBV DNA

Figure 6A:
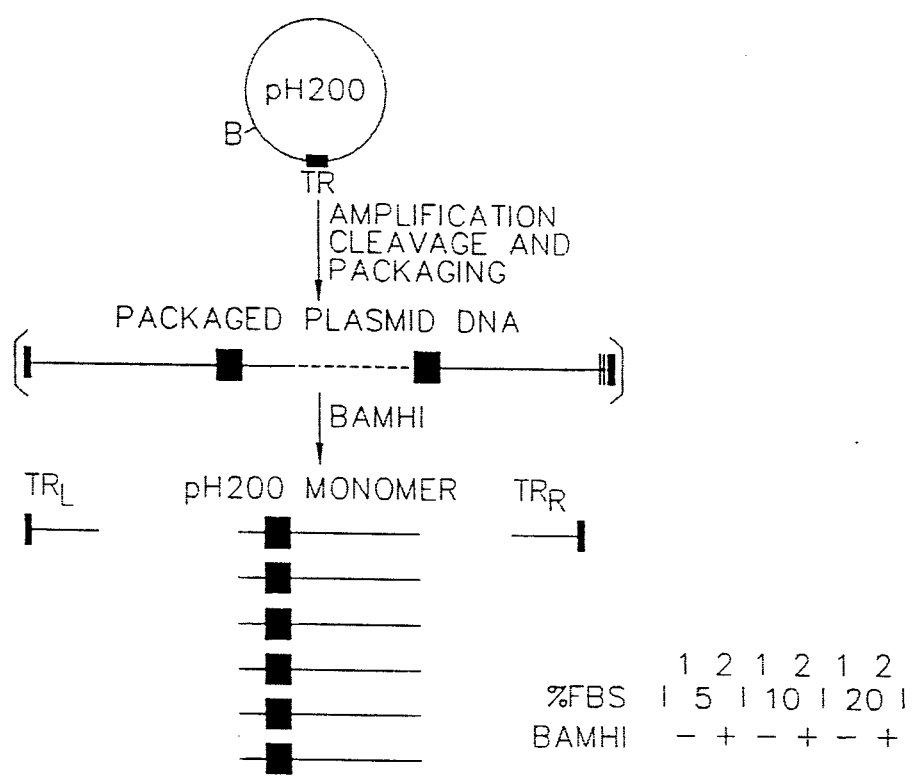
FIGS. 6A and B show the determination of the structure of packaged plasmid-derived DNA. (A) Concatemeric structure of pH200 formed after amplification, cleavage and packaging into virions. During the lytic phase of EBV life cycle, EBV DNA replicates via a rolling-circle mechanism to generate head-to-tail concatemeric DNA molecules, which are then cleaved and packaged into EBV virions. TR is the fused terminal repeats of pH200. The cleavage accompanying packaging yields variable numbers of terminal repeats at left (TR$_L$) and right end (TR$_R$) of packaged DNA. Digestion of a population of linear concatemers of pH200 with BamHI, which cleaves pH200 at one site, yields monomer-size plasmid containing TR and terminal fragments containing the cleaved TR, i.e. TR$_L$ or TR$_R$ (adapted from W. Hammerschmidt and W. Sugden, Nature 340: 393-397 (1989)). (B) Plasmid DNA packaged into virions as unrearranged multimers. The lytic phase of EBV in pH200-transformed HH514 cells grown in 5, 10 and 20% FBS was induced by TPA (20 ng/ml)+butyrate (3 mM). EBV virions and packaged DNA were prepared. Packaged plasmid DNA and helper EBV DNA were detected simultaneously by Southern blot analysis using a pBR322/oriP probe. Lane 1, unrestricted DNA; lane 2, BamHI restricted DNA. Positions of unrestricted linear packaged DNA (pH200 V), linear pH200 plasmid (pH200 M), and oriP fragment of EBV (EBV helper) are indicated at the right. The TR$_L$ or TR$_R$ identifies fragments containing left or right terminal repeat of packaged pH200 concatemers.
Figure 6B:
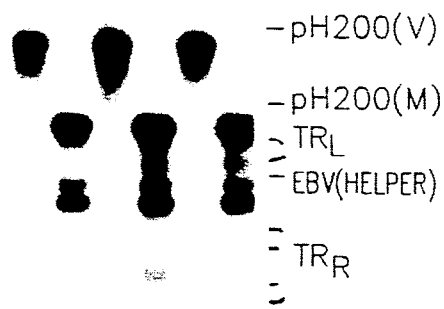

The structure of packaged plasmid-derived DNA was analyzed to determine if sequence rearrangement occurred during amplification and packaging into EBV virions. The structure of packaged plasmid-derived DNA was determined by Southern blot analysis of the purified packaged DNA after cleavage with a single cutter. FIG. 6B shows that the BamHI restricted packaged plasmid-derived DNA (lane 2) generated a strong plasmid monomeric band and several smaller and weaker bands, which are the terminal fragments at left or right end containing TR$_L$ or TR$_R$ sequences (FIG. 6A). The intensities of the monomeric bands relative to the TR bands were consistent with a concatemeric structure of linear plasmid-derived DNA. In confirmation of the PFGE analysis (FIG. 3), this analysis indicated that the packaged plasmid-derived DNA had a head-to-tail concatemeric structure as predicted from a rolling-circle replication. In addition, the analysis of structure of packaged plasmid-derived DNA produced at three different serum concentrations indicated identical restriction patterns; thus, we concluded that the majority of plasmid DNA was unrearranged during amplification and packaging into virions.

EXAMPLE 7

Determination of Packaging Efficiency of Mini EBV DNA

Figure 7:
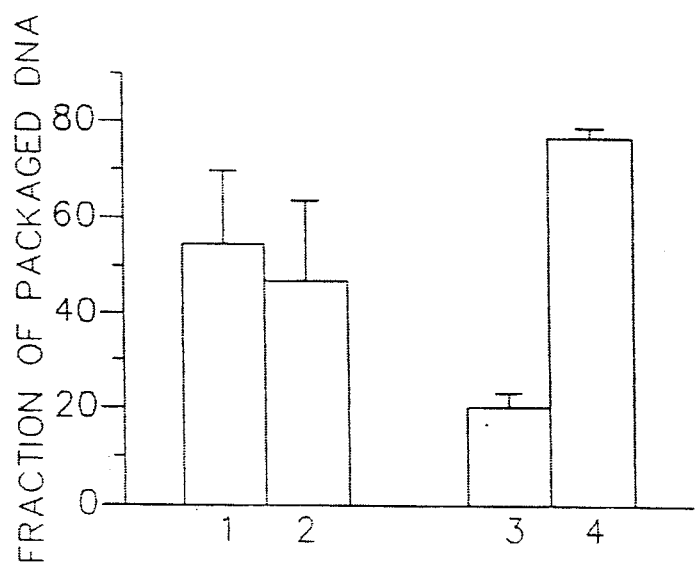
FIG. 7 shows the determination of the packaging efficiency of mini EBV DNA relative to EBV DNA. The fractions of packaged mini EBV and EBV DNA were calculated from PFGE analysis (column 1 and 2) or from restriction analysis (column 3 and 4) as described in FIG. 5 and 6B, respectively. Mini EBV DNA, column 1, 3; EBV DNA, column 2, 4.

The efficiency of packaging of plasmid-derived DNA was determined by comparing the intensities of the plasmid-derived DNA and EBV DNA bands from either the PFGE analysis of FIG. 5 or from the restriction analysis of FIG. 6B. PFGE analysis indicated that 54% of viral stocks were made of mini EBV virions (FIG. 7). A similar result was obtained from the restriction analysis, confirming the conclusion obtained from the PFGE analysis. This result indicated that the engineered mini EBV DNA was packaged into EBV virions with an efficiency similar to that of the resident helper EBV genome.

EXAMPLE 8

Determining Infectivity of Packaged Plasmid DNA

To determine whether the packaged plasmid DNA was infectious, we developed a lacZ-based short term assay for EBV infection. Mini EBV virions were prepared from mini EBV pH210-transformed HH514 cells after induction of the EBV lytic cycle with 20 ng/ml TPA and 1 mM sodium butyrate. The EBV virions were pelleted by centrifugation and resuspended in RPMI-1640 medium without serum. $5 \times 10^6$ cells were resuspended in 0.5 ml concentrated EBV virions containing $8 \times 10^7$ mini EBV virions and incubated for 2 hours at 37° C. Cells were then seeded into 10 ml RPMI-1640 supplemented with 10% FBS and incubated at 37° C. Three days after infection, the infectivity of mini-EBV virions was determined by β-galactosidase assays. In situ identification of the cells expressing β-galactosidase activity was carried out by staining cells with X-gal (5-bromo-4-chloro-3-indolyl-β-galactopyranoside; Sigma). See K. Lim and C.-B. Chae, BioTechniques 7: 576-579 (1989). Whole cell extracts were tested for β-galactosidase activity by incubating with O-nitrophenyl-β-D-galactopyranoside (ONPG) in accordance with known techniques. K. Lim and C.-B. Chae, supra.

Figure 8:
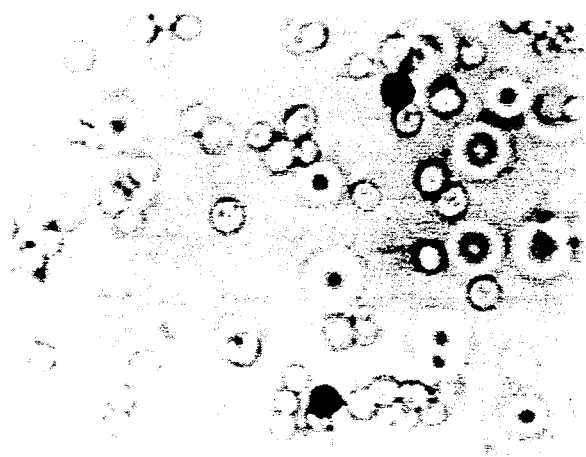
FIG. 8 shows In situ identification of human lymphoblastoid cells infected with mini-EBV/lacZ virions. Raji cells were infected by mini-EBV/lacZ virions prepared from plasmid pH210-transformed HH514 cells. Three days after infection, the cells were incubated with the β-galactosidase substrate X-gal and blue-stained cells were identified under a phase-contrast light microscope at a magnification of 320×.

FIG. 8 shows the in situ identification of infected Raji cells, a human B-lymphoblastoid cell line. Raji cells were successfully infected with the packaged mini EBV and appeared as blue-stained cells. This demonstrated that infectious mini EBV virions carrying an expressible lacZ gene can be produced and used in a short-term infection assay. Efficiencies of EBV-mediated infection and electroporation-mediated DNA transfection in Raji cells were also compared by this assay (Table 1). This analysis showed that mini EBV infection was approximately 3,000-fold more efficient than plasmid transfection in Raji cells.

TABLE 1

DNA Transfer by Infection or Transfection in Raji Cells

|  | Infection | Transfection |
|---|---|---|
| lacZ expression (OD$_{420}$)[a] | 0.2845 | 1.0644 |
| DNA molecules[b] | $8 \times 10^7$ | $9.1 \times 10^{11}$ |
| DNA transfer ($\times 10^{12}$)[c] | 3556 | 1.2 |

[a]The infection and transfection efficiencies were measured as described.
[b]$5 \times 10^6$ cells were infected with $8 \times 10^7$ mini-EBV virions (copy number was determined by DNA hybridization) or transfected with $9.1 \times 10^{11}$ copies of plasmid pH210 DNA (20 ug) by electroporation.
[c]DNA transfer efficiency = $\frac{\text{lacZ expression}}{\text{DNA molecules}}$ Three B-lymphoblastoid cell lines (HSC72, 99, and 230) from three patients suffering from the blood disorder Fanconi's Anemia (FA) were then tested for infection with the packaged mini EBV (Table 2). Two FA cell lines were successfully infected with packaged mini EBV, although with lower efficiency than Raji cells.

TABLE 2

Infectivity of mini-EBV/lacZ+ Virions

| Cell Lines | pH210 Infection[a] (OD at 420 nm) |
|---|---|
| Raji | 0.2845 |

TABLE 2-continued

Infectivity of mini-EBV/lacZ+ Virions

| Cell Lines | pH210 Infection[a] (OD at 420 nm) |
|---|---|
| HSC72 | 0.0805 |
| HSC99 | ND |
| HSC230 | 0.0387 |

[a]Infections were determined as described.
N.D.: Not detectable.

These results indicate that mini EBV/lacZ virions can infect human B-lymphoblastoid cells efficiently including cells from an inherited human syndrome such as FA.

EXAMPLE 9

Establishment of Episomal Library of 150-200 kb Inserts in Human D98/RAJI Cells Partially Bam H1 restricted human genomic DNA is ligated into the EBV plasmid pH210, the plasmid transfected into human D98/RAJI cells by lipofection, and cell transformants selected for hygromycin resistance as described above. Lipofection is carried out with LIPOFECTIN ™ Reagent Catalog No. 8292SA obtained from Bethesda Research Laboratories/Life Technologies, Inc., Gaithersburg, Md., USA (Tel. (800) 638-4045/(301) 840-8000) in accordance with known techniques and as recommended in the manufacturer's package insert (see also P. Felgner et al., Proc. Natl. Acad. Sci. USA 84, 7413 (1987); Focus 11, 13 (1989) C. Gorman et al., Mol. Cell Biol. 2, 1044 (1982); A. Chang and D. Brenner, Focus 10, 66 (1988), modified as follows:

DAY 1: seed $3-5 \times 10^5$ cells in 3 ml growth medium to each well of a six well plate.

DAY 2: (A) prepare DNA-liposome complex. Add 5 μg DNA into 1.5 ml of OPTI-MEM ™ medium (Gibco, Laboratories) in a polystyrene tube. Dilute 20 μl LIPOFECTIN ™ lipofection reagent in 1.5 ml OPTI-MEM ™ medium in a separate polystyrene tube, then mix DNA and liposome dilution gently in a polystyrene tube (total 3 ml) and let stand for 15 minutes at room temperature. (B) Meanwhile, wash cells grown on the six-well plate with PBS three times and add 3 ml of DNA-liposome mixture to cells grown on one well. (C) Incubate cells in incubator for 12-18 hours, then remove DNA-liposome, and add 3 ml growth medium such as EMEM supplemented with 10% FBS.

DAY 3: Trypsinize cells and seed into a 100 mm dish.

Figure 9:
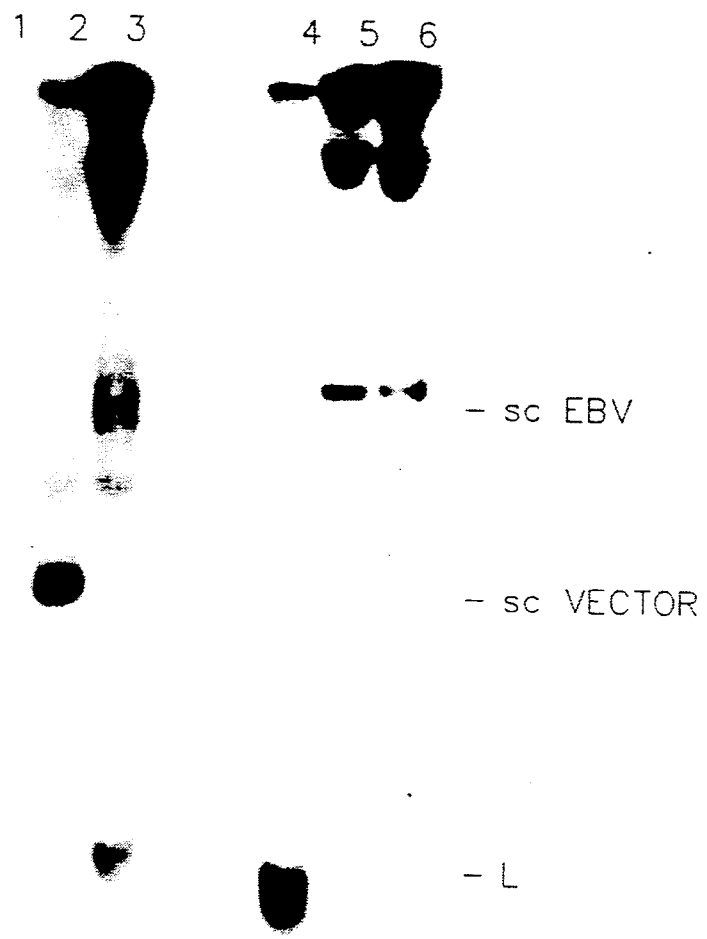
FIG. 9 shows the detection of episomal pH210 containing 150-200 kb human genomic DNA inserts: supercoiled episomal DNA was prepared by alkali lysis. Circular DNA was fractionated on 1% TBE agarose gel and Southern hybridized with a probe specific for either pH210 (lanes 1-3) or EBV (lanes 4-6); Lanes 1,4: EBV prepared from control helper cells; lanes 2,5: pH21 plasmid prepared from control cells; lanes 3,6: episomal pH210 containing 150-200 kb human genomic DNA inserts prepared from transformed helper cells. The positions of supercoiled circular EBV (sc EBV), of linear EBV (L) and of supercoiled circular vector (SC vector) are indicated on the right.

Three weeks after transfection, Southern blot analysis performed on low-molecular weight DNA extracted by alkali-lysis using an Alu probe indicates that the introduced plasmid is maintained as a circular episome in the D98/RAJI transformants at approximately the same size as the resident EBV (FIG. 9).

EXAMPLE 10

Figure 10:
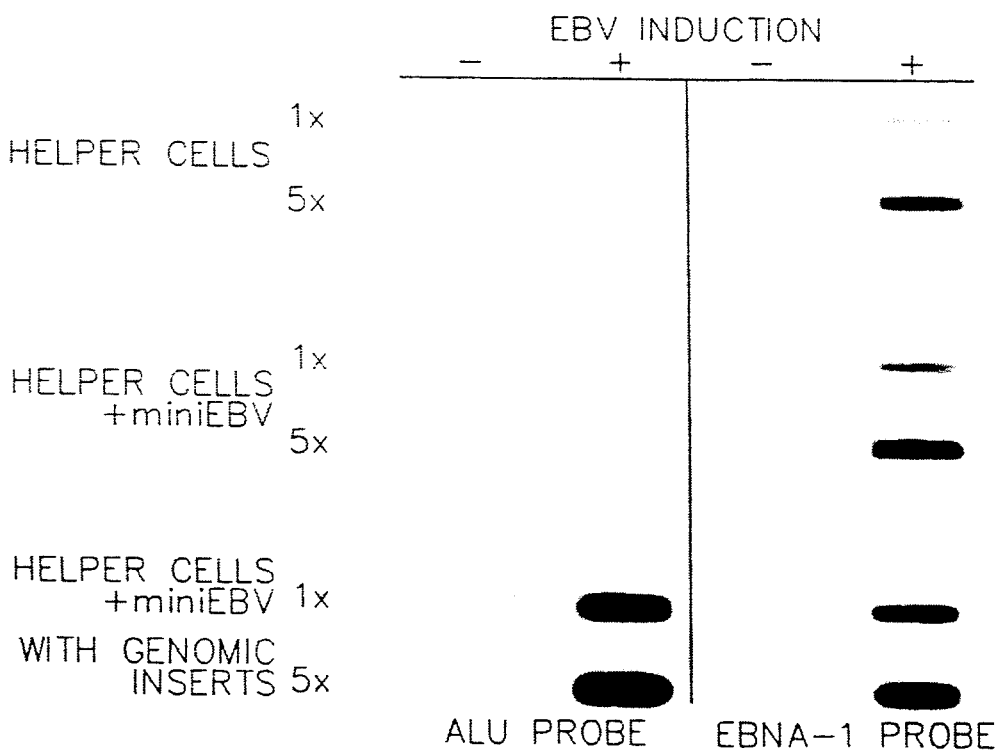
FIG. 10 shows that EBV virions can package 150-200 kb human genomic inserts through slot blot hybridization of viral packaged DNA prepared from helper cells carrying EBV plasmid pH210 and helper cells carrying EBV plasmid pH210 containing 150-200 kb human genomic DNA inserts. 1× and 5×, 1-fold and 5-fold samples were loaded. Alu: human genomic specific probe; EBNA-1 probe: EBV specific probe.

Detection of 150-200 kb Human Genomic DNA in EBV virions by Slot-Blot Hybridization Viral packaged DNA is prepared by EBV lytic induction of the cell transformants prepared in Example 9 as described above and analyzed by slot-blot hybridization with a human specific probe (Alu) and an EBV specific probe (EBNA-1). Data are shown in FIG. 10.

These data confirm the successful packaging of 150-200 kb genomic DNA into EBV virions.

EXAMPLE 11

Figure 11:
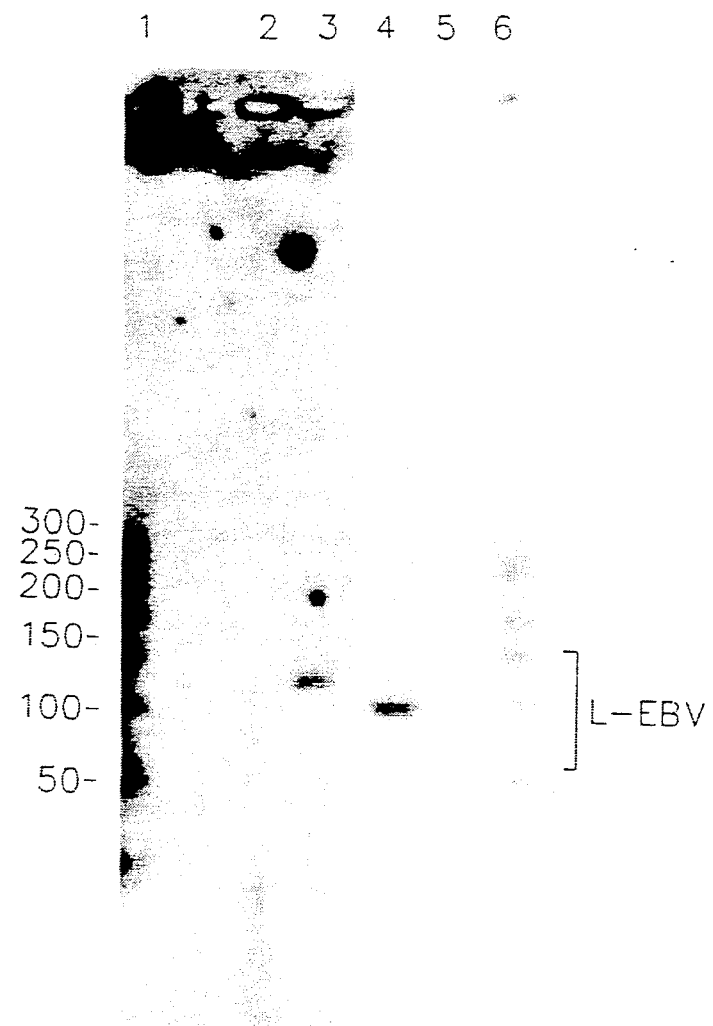
FIG. 11 shows Pulse-Field Gel Electrophoresis (PFGE) analysis of EBV virions carrying 150-200 kb inserts: EBV is induced from helper cells carrying the pH210-based episomal human genomic library. Viral DNA is run on PGFE and analyzed by Southern blot with probes specific for either human DNA (lanes 2,4) or the EBV (lanes 3,5). Lanes 1,6 are lambda concatemers; lanes 2,4 and 3,6 correspond to two different viral stock preparations. L-EBV indicates the position of pH210 EBV virions with the human DNA inserts.

Detection of 150-200 kb Human Genomic DNA in EBV Virions by Pulse-Field Gel Electrophoresis D98/RAJI cells transformed with episomal pH210 and carrying 150-200 kb human genomic inserts is treated with either TPA, TPA and butyrate, or electroporated with the BZLF-1 gene expressed from a CMV promoter. Five days later, the virus released in the culture medium is collected and purified from any plasmid contaminant. DNA extracted from the virions is separated by PFGE and analyzed by Southern hybridization using an Alu probe. As illustrated by FIG. 11, pH210 virions produced from these cells migrate and have a similar position as the helper EBV, indicating that large human genomic DNA inserts are packaged into the EBV virions.

The foregoing examples are illustrative of the present invention, and are not to be construed as limiting thereof. The invention is defined by the following claims, with equivalents of the claims to be included therein.

That which is claimed is:

1. A recombinant plasmid useful for the production of large-insert episomes in mammalian cells, comprising:
   a lymphotrophic herpes virus segment which (a) contains an origin of plasmid replication (oriP) and (b) is maintained as an episome in a mammalian host cell; and
   a heterologous insert segment linked to said lymphotrophic herpes virus segment, said heterologous insert segment having a length of at least 100 kilobases.

2. A recombinant plasmid according to claim 1, wherein said lymphotrophic herpes virus segment is capable of producing infectious virions in a suitable host cell, and wherein said lymphotrophic herpes virus segment has regions deleted so that said recombinant plasmid retains the capability of producing infectious virions in said host cell.

3. A recombinant plasmid according to claim 1, wherein said heterologous insert segment has a length of at least 120 kilobases.

4. A recombinant plasmid according to claim 1, wherein said heterologous insert segment has a length of at least 150 kilobases.

5. A recombinant plasmid according to claim 1, said heterologous insert segment including a centromere operable in said host cell.

6. A recombinant plasmid according to claim 1, wherein said lymphotrophic herpes virus segment comprises an Epstein-Barr virus segment.

7. A recombinant plasmid according to claim 1, wherein said lymphotrophic herpes virus segment has regions deleted which render said recombinant plasmid capable of producing infectious virions only in a host cell containing helper sequences.

8. A method for transforming mammalian cells, said method comprising transfecting a mammalian cell with a recombinant plasmid, said recombinant plasmid comprising:
   a lymphotrophic herpes virus segment which (a) contains an origin of plasmid replication (oriP) and (b) is maintained as an episome in a mammalian cell; and
   a heterologous insert segment linked to said lymphotrophic herpes virus segment, said heterologous insert segment having a length of at least 100 kilobases.

9. A method according to claim 8, wherein said lymphotrophic herpes virus segment is capable of producing infectious virions in a suitable host cell, and wherein said lymphotrophic herpes virus segment has regions deleted so that said recombinant plasmid retains the capability of producing infectious virions in said host cell.

10. A method according to claim 8, wherein said mammalian cells are grown as a monolayer in in vitro cell culture, and wherein said transfecting step is carried out by lipofection.

11. A method according to claim 8, wherein said mammalian cell is a B-lymphoblastoid cell.

12. A method according to claim 8, wherein said mammalian cell is a fusion of a mammalian epithelial cell and a mammalian B-lymphoblastoid cell.

13. A method according to claim 8, wherein said mammalian cell is an epithelial cell.

14. A method according to claim 8, said heterologous insert segment including a centromere operable in said mammalian cell.

15. A method according to claim 8, wherein said mammalian cell is capable of producing infectious virions from said recombinant plasmid.

16. A method according to claim 8, wherein said mammalian cell is incapable of producing infectious virions from said recombinant plasmid.

17. A transformed mammalian cell containing a recombinant plasmid, said recombinant plasmid comprising:
   a lymphotrophic herpes virus segment which (a) contains an origin of plasmid replication (oriP) and (b) is maintained as an episome in said mammalian cell; and
   a heterologous insert segment linked to said lymphotrophic herpes virus segment, said heterologous insert segment having a length of at least 100 kilobases.

18. A transformed mammalian cell as claimed in claim 17, wherein said lymphotrophic herpes virus segment is capable of producing infectious virions in a suitable host cell, and wherein said lymphotrophic herpes virus segment has regions deleted so that said recombinant plasmid retains the capability of producing infectious virions in said suitable host cell.

19. A transformed mammalian cell according to claim 17, said heterologous insert segment including a centromere operable in said mammalian cell.

20. A transformed mammalian cell as claimed in claim 17, wherein said cell is grown as a monolayer in in vitro cell culture.

21. A transformed mammalian cell according to claim 17, wherein said cell is a human cell.

22. A transformed mammalian cell according to claim 17, wherein said cell is capable of producing infectious virions from said recombinant plasmid.

23. A transformed mammalian cell according to claim 17, wherein said cell is a B-lymphoblastoid cell.

24. A transformed mammalian cell according to claim 17, wherein said cell is a fusion of a mammalian epithelial cell and a mammalian B-lymphoblastoid cell.

25. A transformed mammalian cell according to claim 17, wherein said cell is an epithelial cell.

26. A transformed mammalian cell according to claim 17, wherein said heterologous insert segment has a length of at least 120 kilobases.

27. A transformed mammalian cell according to claim 17, wherein said heterologous insert segment has a length of at least 150 kilobases.

28. A transformed mammalian cell according to claim 17, wherein said lymphotrophic herpes virus segment comprises an Epstein-Barr virus segment.

29. A large insert DNA library comprising a plurality of transformed mammalian cells, each of said transformed mammalian cells containing a recombinant plasmid, said recombinant plasmid comprising:
- a lymphotrophic herpes virus segment which (a) contains an origin of plasmid replication (oriP) and (b) is maintained as an episome in said mammalian cell; and
- a heterologous insert segment linked to said lymphotrophic herpes virus segment, said heterologous insert segment having a length of at least 100 kilobases and comprising a member of said DNA library.

30. A large-insert DNA library according to claim 29, said lymphotrophic herpes virus segment having regions deleted so that said recombinant plasmid retains the capability of producing infectious virions in a suitable host cell.

31. A large-insert DNA library according to claim 29, wherein said library is a human genomic DNA library, and wherein said mammalian cells are human cells.

32. A large-insert DNA library according to claim 29, wherein said lymphotrophic herpes virus segment is an Epstein-Barr virus segment, and wherein said mammalian cells are human B-lymphoblastoid cells.

33. A large-insert DNA library according to claim 29, wherein said library is a partial genomic DNA library.

34. A large-insert DNA library according to claim 29, wherein said library is a complete genomic DNA library.

35. A large-insert DNA library comprising a plurality of infectious lymphotrophic herpes virus virions, each of said virions containing a recombinant DNA molecule, said recombinant DNA molecule comprising:
- a lymphotrophic herpes virus segment which is capable of infecting mammalian cells, is maintained as an episome therein, and produces infectious virions in a suitable host; and
- a heterologous insert segment linked to said lymphotrophic herpes virus segment, said heterologous insert segment having a length of at least 100 kilobases and comprising a member of said DNA library;
- said lymphotrophic herpes virus segment having regions deleted so that said recombinant DNA sequence retains the capability of producing infectious virions in a suitable host;
- said lymphotrophic herpes virus segment including an origin of plasmid replication (oriP), a lytic origin of replication (oriLyt), and long terminal repeat regions (TR).

36. A large-insert DNA library according to claim 35, wherein said library is a human genomic DNA library.

37. A large-insert DNA library according to claim 35, wherein said lymphotrophic herpes virus segment is an Epstein-Barr virus segment.

38. A large-insert DNA library according to claim 35, wherein said library is a partial genomic DNA library.

39. A large-insert DNA library according to claim 35, wherein said library is a complete genomic DNA library.

40. A recombinant plasmid useful for the production of large-insert episomes in mammalian cells, comprising:
- an Epstein-Barr virus segment containing an origin of plasmid replication (oriP), a lytic origin of replication (oriLyt), and a fused long terminal repeat region (TR); and
- a heterologous insert segment linked to said Epstein-Barr virus segment, said heterologous insert segment having a length of at least 100 kilobases.

41. A method for transforming mammalian cells, said method comprising transfecting a mammalian cell with a recombinant plasmid of claim 40.

42. A transformed mammalian cell containing a recombinant plasmid according to claim 40.

43. A large-insert DNA library comprising a plurality of transformed mammalian cells, each of said transformed mammalian cells containing a recombinant plasmid according to claim 40.

44. An infectious lymphotrophic herpes virus virion containing a recombinant DNA molecule, said recombinant DNA molecule comprising:
- a lymphotrophic herpes virus segment which is capable of infecting mammalian cells, is maintained as an episome therein, and produces infectious virions in a suitable host; and
- a heterologous insert segment linked to said lymphotrophic herpes virus segment, said heterologous insert segment having a length of at least 100 kilobases;
- said lymphotrophic herpes virus segment having regions deleted so that said recombinant DNA sequence retains the capability of producing infectious virions in a suitable host;
- said lymphotrophic herpes virus segment including an origin of plasmid replication (oriP), a lytic origin of replication (oriLyt), and long terminal repeat regions (TR).

45. An infectious lymphotrophic herpes virus virion according to claim 44, wherein said lymphotrophic herpes virus segment is an Epstein-Barr virus segment.

46. An infectious lymphotrophic herpes virus virion according to claim 44, wherein said heterologous insert segment has a length of at least 120 kilobases.

47. An infectious lymphotrophic herpes virus virion according to claim 44, wherein said heterologous insert segment has a length of at least 150 kilobases.

48. An infectious lymphotrophic herpes virus virion according to claim 44, said heterologous insert segment including a centromere operable in a mammalian cell.

* * * * *